United States Patent
Isozaki et al.

(10) Patent No.: US 7,064,820 B2
(45) Date of Patent: Jun. 20, 2006

(54) SURFACE INSPECTION METHOD AND SURFACE INSPECTION SYSTEM

(75) Inventors: Hisashi Isozaki, Tokyo-to (JP); Michihiro Yamazaki, Tokyo-to (JP); Hiroshi Yoshikawa, Tokyo-to (JP); Naoto Miki, Tokyo-to (JP); Hiroyuki Maekawa, Tokyo-to (JP); Naohiro Takahashi, Kawasaki (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 288 days.

(21) Appl. No.: 10/393,833

(22) Filed: Mar. 21, 2003

(65) Prior Publication Data

US 2003/0184744 A1   Oct. 2, 2003

(30) Foreign Application Priority Data

Mar. 27, 2002 (JP) ............................. 2002-088555

(51) Int. Cl.
*G01N 21/00* (2006.01)
*G01J 4/00* (2006.01)

(52) U.S. Cl. .................................. 356/237.2; 356/369

(58) Field of Classification Search .. 356/237.1–237.5, 356/241.1–241.6, 238.1–238.3, 240.1, 369, 356/370; 250/559.4–559.45; 382/141, 145, 382/148, 149, 126, 129, 125

See application file for complete search history.

(56) References Cited

U.S. PATENT DOCUMENTS

| | | | | |
|---|---|---|---|---|
| 4,386,850 A | * | 6/1983 | Leahy | ...................... 356/243.4 |
| 4,614,427 A | * | 9/1986 | Koizumi et al. | .......... 356/237.1 |
| 5,179,422 A | | 1/1993 | Peterson | ..................... 356/239 |
| 6,628,381 B1 | * | 9/2003 | Komem et al. | .......... 356/237.4 |
| 6,797,975 B1 | * | 9/2004 | Nishiyama et al. | .... 250/559.04 |

FOREIGN PATENT DOCUMENTS

JP        2001-208697         8/2001

* cited by examiner

*Primary Examiner*—Layla G. Lauchman
*Assistant Examiner*—Gordon J. Stock, Jr.
(74) *Attorney, Agent, or Firm*—Nields & Lemack (57) ABSTRACT

A surface inspection method in a surface inspection system which comprises a photodetection unit and a photodetection polarizing angle changing means, comprising the step of receiving a scattered reflection light from a substrate surface where standard particles are coated by changing a photodetection polarizing angle by the photodetection polarizing angle changing means, and the step of performing surface inspection by setting the photodetection polarizing angle to a condition where an S/N ratio of photodetection output is at the highest.

4 Claims, 5 Drawing Sheets

SURFACE INSPECTION METHOD AND SURFACE INSPECTION SYSTEM

CROSS-REFERENCE TO RELATED APPLICATIONS

This application is based upon and claims the benefit of priority from the prior Japanese Patent Application No. 2002-88555, filed on Mar. 27, 2002, the entire contents of which are incorporated herein by reference.

BACKGROUND OF THE INVENTION

The present invention relates to a surface inspection method and a surface inspection system for detecting foreign objects on a surface of a substrate such as a wafer.

In the manufacture of a semiconductor device, fine foreign objects spread on a surface of a substrate such as a wafer exerts extensive influence on the quality of the product. For this reason, surface inspection is performed on the surface of the substrate in the process to manufacture the semiconductor device. The semiconductor devices with increasingly high density are now produced, and the manufacturing process is also becoming more and more complicated. Moreover, various types of films are formed on the surface of the wafer.

A surface inspection system detects foreign objects by projecting an inspection light to the surface of the substrate and by receiving a scattered reflection light from the substrate using a photodetector. In the reflection light from the substrate, reflection characteristics vary according to film quality and film thickness of the film formed on the substrate surface. For this reason, in order to improve an S/N ratio and to increase detection accuracy of the surface inspection, it is necessary to set an inspection condition to correspond to film quality.

The reflection light detected by the photodetector contains not only the scattered reflection light from foreign objects but also a scattered reflection light from the surface of the substrate itself. The scattered reflection light of the substrate surface itself is turned to noise and decreases the detection accuracy in the detection of foreign objects.

JP-A-2001-208697 discloses a surface inspection system, which provides higher detection accuracy by removing the scattered reflection light from the substrate surface itself.

The invention of JP-A-2001-208697 is based on the fact that, when a laser beam is projected to a substrate and it is reflected, condition of polarization is changed due to scattered reflection from the substrate surface. When an S-polarized laser beam is projected to the substrate, an elliptically polarized laser beam is reflected from the substrate surface. A polarizing plate is arranged on a photodetection system, and the scattered reflection light is received through the polarizing plate. By rotating the polarizing plate, a condition is obtained where a photodetection level of the photodetector is at the lowest (i.e. a condition where the reflection light on the substrate surface is at the lowest). The polarizing plate is positioned at a rotating position under this condition, and surface inspection of the substrate is carried out.

The scattered reflection light from the substrate surface is reduced by the polarizing plate, and a ratio of the scattered reflection light from foreign objects to the scattered reflection light from the substrate surface (i.e. S/N ratio) is increased, and this leads to higher detection accuracy.

It is already known that the scattered reflection light on the substrate surface contains a plurality of polarization components depending on the types of the films formed on the substrate surface. In this case, by such method as to eliminate the influence of the reflection light by finding the rotating position of the polarizing plate where the scattered reflection light from the substrate surface is at the lowest as in the case of the conventional type surface inspection system, there are two or more rotating positions of the polarizing plate where the scattered reflection light from the substrate surface is at the minimal value. Further, it is already known that an amount of detected light of the scattered reflection light from foreign objects is also influenced by the rotating position of the polarizing plate. In this respect, sufficient detection accuracy cannot be attained in the surface inspection of foreign objects by simply rotating the polarizing plate and by performing inspection under the condition where the scattered reflection light on the substrate surface is at the lowest.

SUMMARY OF THE INVENTION

It is an object of the present invention to provide a surface inspection method and a surface inspection system, by which it is possible to improve S/N ratio of a photodetection reflection light and to carry out surface inspection with higher accuracy.

To attain the above object, the present invention provides a surface inspection method in a surface inspection system, which comprises a photodetection unit and a photodetection polarizing angle changing means, comprising the step of receiving a scattered reflection light from a substrate surface where standard particles are coated by changing a photodetection polarizing angle by the photodetection polarizing angle changing means, and the step of performing surface inspection by setting the photodetection polarizing angle to a condition where an S/N ratio of photodetection output is at the highest. Also, the present invention provides the surface inspection method as described above, wherein the highest value of the S/N ratio is determined based on a standard particle scattering output and a substrate surface scattering output. Further, the present invention provides the surface inspection method as described above, wherein the highest value of the S/N ratio is obtained when the minimal value and the maximal value in a histogram are clearly separated from each other. Also, the present invention provides the surface inspection method as described above, wherein it is judged that the S/N ratio is the highest value when a ratio of the minimal value to the maximal value is 0.7 or more. Further, the present invention provides a surface inspection system, which comprises a projecting optical system for projecting an inspection light to a surface to be inspected, a photodetection unit for receiving a scattered reflection light from the surface to be inspected having foreign objects thereon, a photodetection polarizing angle changing means arranged on a photodetection optical axis and for changing a photodetection polarizing angle of the photodetection unit, and an arithmetic unit for calculating a photodetection polarizing angle of the photodetection polarizing angle changing means where an S/N ratio is at the highest based on a photodetection output from the photodetection unit obtained by changing the photodetection polarizing angle by the photodetection polarizing angle changing means. Also, the present invention provides the surface inspection system as described above, wherein the arithmetic unit obtains a histogram at each photodetection polarizing angle respectively by changing the photodetection polarizing angle, calculates a point where a ratio of the minimal value to the maximal value is at the highest by comparing the histogram thus obtained, and calculates the photodetection polarizing angle of the photodetection polarizing angle changing means. Further, the present invention provides the surface inspection system as described above, wherein an inspection light is projected at a predetermined angle to the surface to be inspected, a scattered reflection light from foreign objects and a scattered reflection light from the surface to be inspected itself are detected by the photodetection unit respectively, and the arithmetic unit calculates the photodetection polarizing angle of the photodetection polarizing angle changing means where the S/N ratio is at the highest based on a scattered reflection light output from the foreign objects and on a scattered reflection light output from the surface to be inspected itself. Also, the present invention provides the surface inspection system as described above, wherein it is judged that the S/N ratio is the highest when a ratio of the minimal value to the maximal value is 0.7 or more.

DETAILED DESCRIPTION OF THE PREFERRED EMBODIMENT

Description will be given below on an embodiment of the present invention referring to the drawings.

Figure 1:
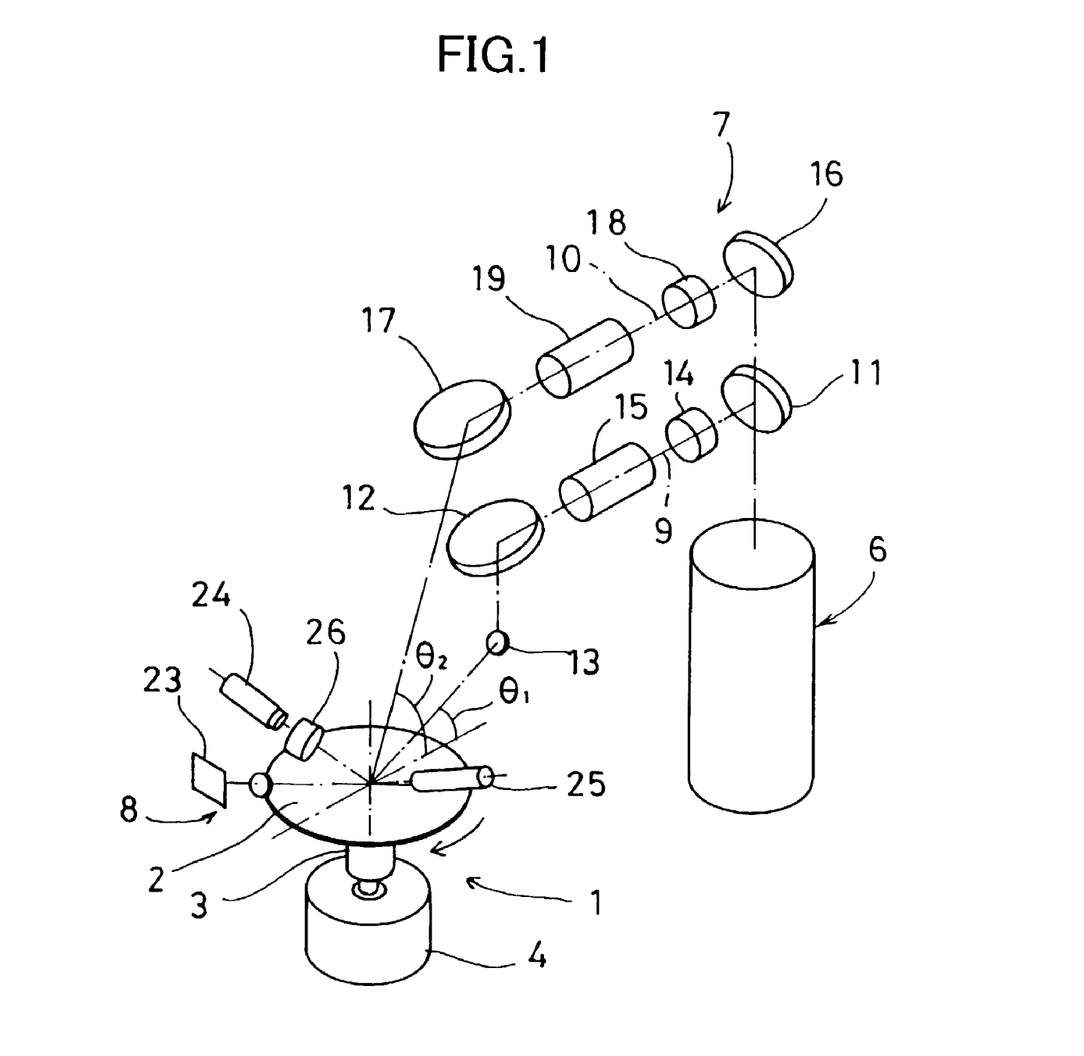
FIG. 1 is a perspective view of an essential portion of an embodiment of the present invention.

FIG. 1 shows basic arrangement of a surface inspection system.

In the figure, reference numeral 1 denotes a substrate scanning mechanism. The substrate scanning mechanism 1 comprises a wafer chuck 3 for holding a substrate (wafer) 2, and a rotating motor 4 for rotating the wafer chuck 3. The rotating motor 4 is mounted on a slide stage 20 (See FIG. 2) moving in a horizontal direction, and the slide stage 20 is moved in a horizontal direction by a sliding motor 21 (See FIG. 2).

In the figure, reference numeral 6 represents a laser beam emitter, 7 is a projecting optical system, and 8 is a photodetection unit. A laser beam emitted from the laser beam emitter 6 is projected to a surface of the wafer 2 by the projecting optical system 7.

FIG. 1 shows an example of the projecting optical system 7, which is designed in such manner that a laser beam 9 projected at a low incident angle θ1 and a laser beam 10 projected at a high incident angle θ2 are provided by the common laser beam emitter 6.

The projecting optical system 7 projects the two laser beams 9 and 10 onto the wafer 2 at predetermined incident angles.

The laser beam 9 is deflected by deflecting optical members 11, 12 and 13 such as mirrors so as to enter the surface of the wafer 2 at the predetermined incident angle θ1. The form of the light beam is adjusted by a beam expander 14 and the light beam is converged to the surface of the wafer 2 by a lens group 15.

The laser beam 10 is deflected by deflecting optical members 16 and 17 such as mirrors so as to enter the surface of the wafer 2 at the predetermined angle θ2. The form of the light beam is adjusted by a beam expander 18 and the light beam is converged to the surface of the wafer 2 by a lens group 19.

Figure 2:
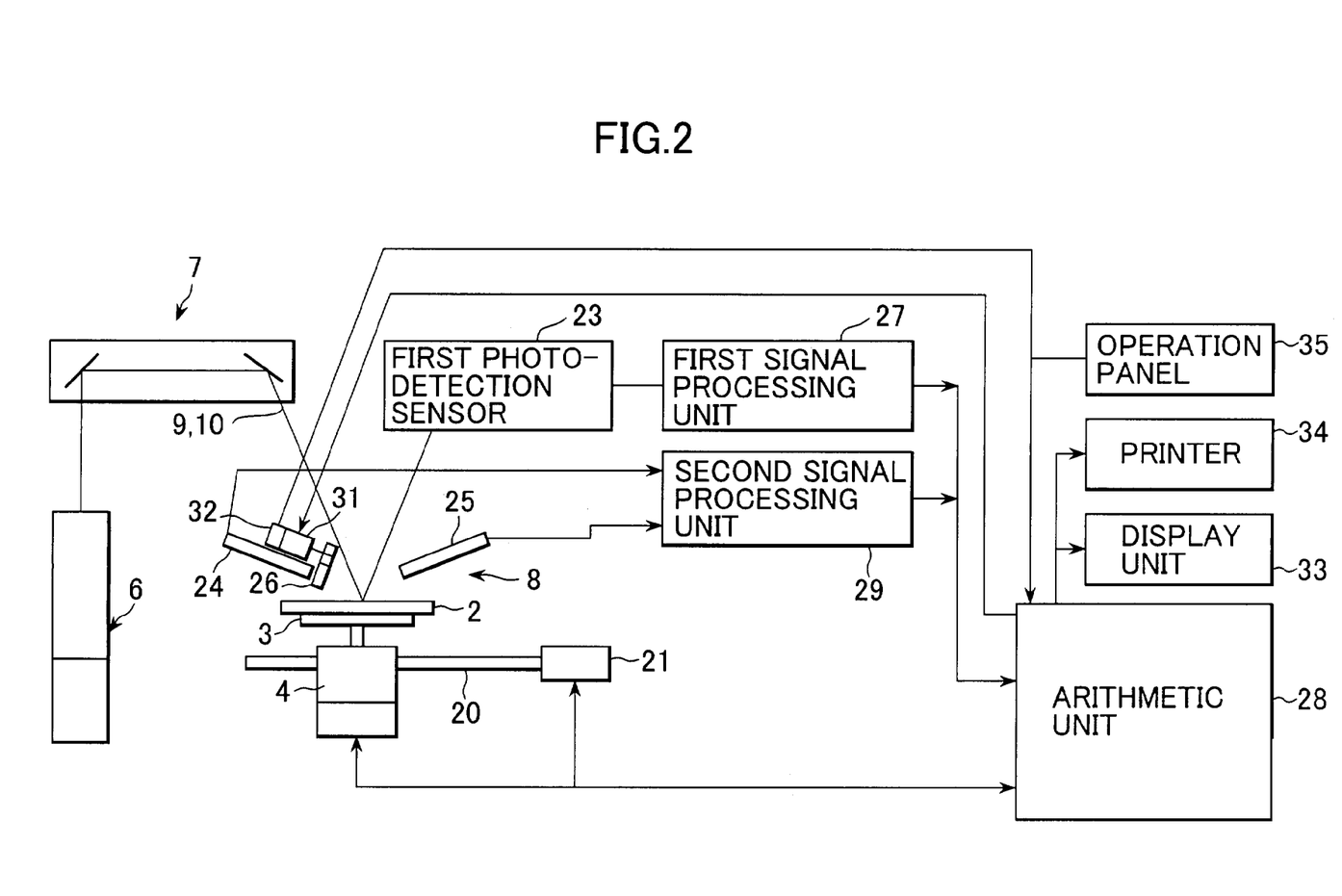
FIG. 2 is a block diagram showing the above embodiment.

The photodetection unit 8 comprises a first photodetection sensor 23, a second photodetection sensor 24, and a third photodetection sensor 25. The first photodetection sensor 23 receives a direct reflection light of the laser beam 9 and the laser beam 10 reflected by the surface of the wafer 2, and detects a position of the wafer 2 in a height direction. The second photodetection sensor 24 and the third photodetection sensor 25 are arranged at such predetermined positions that the scattered reflection light is received when the laser beam 9 and the laser beam 10 are reflected with scattering reflection on the surface of the wafer 2. On a photodetection optical axis of the second photodetection sensor 24, a polarizing plate 26 is rotatably retained. The polarizing plate 26 can be rotated by a photodetection polarizing angle setting motor 31 such as an AC servomotor, a stepping motor, etc., which can control a rotating position of the polarizing plate 26. A photodetection polarizing angle of the polarizing plate 26 is detected by an angle detector 32, and the photodetection polarizing angle thus detected is inputted to an arithmetic unit 28. The polarizing plate 26 may be arranged on a photodetection optical axis of the third photodetection sensor 25.

The reflection light received at the first photodetection sensor 23 is converted to an electric signal. After being processed by required processing procedure such as being amplified and processed by A/D conversion on the first signal processing unit 27, the electric signal is inputted to the arithmetic unit 28. At the arithmetic unit 28, the position of the wafer 2 in the height direction is calculated based on the signal from the first signal processing unit 27.

The scattered reflection light received at the second photodetection sensor 24 and the third photodetection sensor 25 is amplified at a second signal processing unit 29. After being processed by required processing procedure such as A/C conversion, the signal is inputted to the arithmetic unit 28.

At the smaller incident angle θ1, the influence of foreign objects to the scattered reflection light is higher. At the larger incident angle θ2, the influence to the scattering reflection on the surface of the wafer 2 is higher. Therefore, if the incident angle of the inspection light is adequately selected and results of photodetection at the second photodetection sensor 24 and the third photodetection sensor 25 are obtained, it is possible to find a scattered reflection component of the photodetection signal on the surface of the wafer 2, i.e. a noise component, or a scattered reflection component from foreign objects, i.e. a signal component.

In FIG. 2, reference numeral 33 represents a display unit, 34 is a printer, and 35 is an operation panel.

Now, description will be given on surface inspection of a substrate by the surface inspection system with the arrangement as described above.

First, description will be given on general outline of operation of a mechanical part during surface inspection.

With the laser beam 9 or the laser beam 10 or both of these laser beams being projected to the wafer 2, the wafer 2 is rotated at a constant speed by the rotating motor 4. Further, the slide stage 20 is moved at a constant speed by the sliding motor 21. By the rotation of the wafer 2 and by the movement of the slide stage 20, a projecting point of the laser beam 9 or the laser beam 10 is moved to scan over the entire surface of the wafer 2 in a spiral manner. The first photodetection sensor 23 receives the reflection light from the surface of the wafer 2 while scanning, and the second photodetection sensor 24 and the third photodetection sensor 25 receive the scattered reflection lights from the surface of the wafer 2. Then, the photodetection signal is inputted to the arithmetic unit 28 via the second signal processing unit 29 and the first signal processing unit 27. By providing an ND filter (not shown) in an optical path, detection sensitivity to the scattered reflection light of each of the second photodetection sensor 24 and the third photodetection sensor 25 can be switched over to high sensitivity and low sensitivity.

The polarizing plate 26 is rotated in the present surface inspection system. The polarizing plate 26 is retained at a rotating position where a signal ratio (S/N ratio) of the scattered reflection component due to foreign objects reaches the maximum, and surface inspection is performed.

The rotating position of the polarizing plate 26 is determined in a process for setting inspection condition, i.e. in the preceding stage before the surface inspection.

A wafer for calibration is prepared, on which foreign objects (particles) of particle size already known are spread at a known density. As the wafer for calibration, a wafer is used, which has the film type and the film thickness, etc. matching with the wafer to be inspected.

As described above, in the scattered reflection light from foreign objects and the scattered reflection light from the substrate surface, the amount of receiving light varies according to the photodetection polarizing angle of the polarizing plate 26 when the light is received through the polarizing plate 26 arranged on the optical axis of the reflection light.

Figure 3:
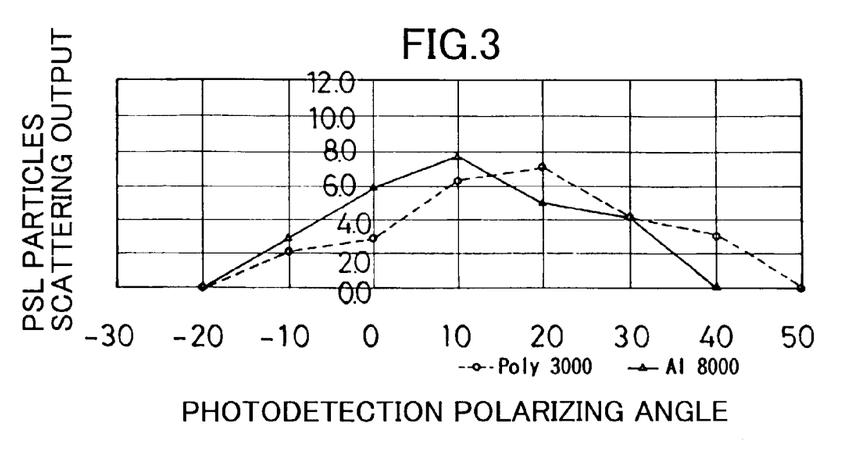
FIG. 3 is a diagram showing conditions of a scattered reflection light from PSL particles (standard particles) and a photodetection polarizing angle.
Figure 4:
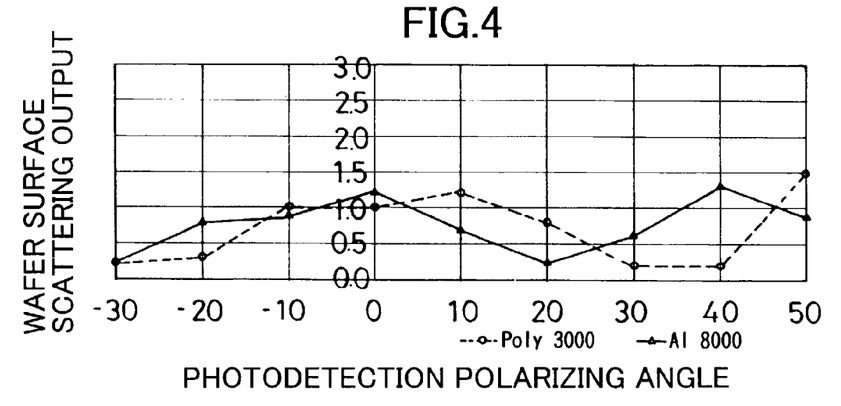
FIG. 4 is a diagram showing conditions of a scattered reflection light from a surface of a wafer and a photodetection polarizing angle.

FIG. 3 and FIG. 4 each represents relationship between the photodetection polarizing angle (obtained by rotating the polarizing plate 26 of the photodetection unit 8) and photodetection output of the second photodetection sensor 24. In FIG. 3 and FIG. 4, solid lines show the values when the film formed on the wafer surface is Al 8000, and dotted lines show the values when the film is Poly 3000. Alphabetic symbols on the beginning parts of Al 8000 and Poly 3000 (i.e. Al and Poly) show materials of the film respectively. The numerical values on the latter parts show film thickness using Angstrom as an unit.

FIG. 3 shows PSL particles scattering output, which is the photodetection output of the second photodetection sensor 24 based on the scattered reflection light from PSL particles (standard particles). From the diagram, it is evident that the maximal value appears when the photodetection polarizing angle of Al 8000 and Poly 3000 are 10° and 20° respectively.

FIG. 4 shows wafer surface scattering output, which is the photodetection output of the second photodetection sensor 24 based on the scattered reflection light from the surface of the wafer for calibration. In case of Al 8000, the minimal value appears respectively when the photodetection polarizing angle is −30° or lower, at 20°, and 50° or more. In case of Poly 3000, the minimal values appear respectively when the photodetection polarizing angle is at −30° and between 30° and 40°.

When the results shown in FIG. 3 and FIG. 4 are compared, in both cases of Al 8000 and Poly 3000, the photodetection polarizing angle where the maximal value appears and the photodetection polarizing angle where the minimal value appears are not consistent with each other. Further, it is evident that the minimal values appear repeatedly.

Figure 5:
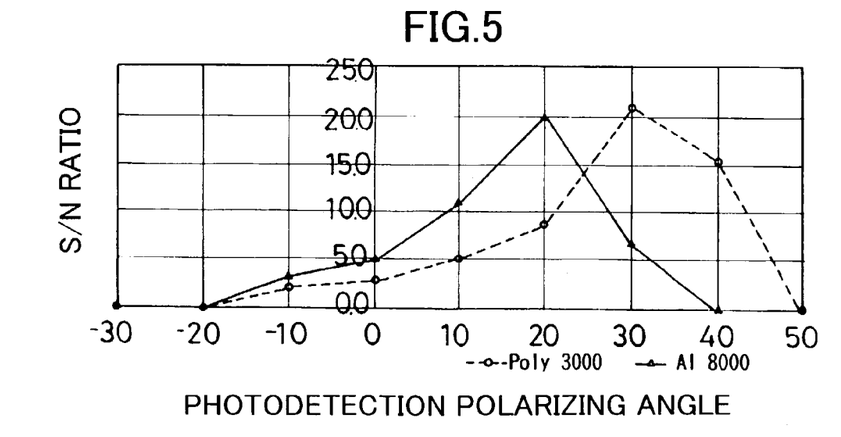
FIG. 5 is a diagram showing conditions of a photodetection output ratio of a scattered reflection light from PSL particles (standard particles) to a scattered reflection light from the wafer surface and a photodetection polarizing angles.

Next, FIG. 5 shows PSL particles/wafer surface scattering output ratio (S/N ratio) prepared based on the results of detection in FIG. 3 and FIG. 4. In the diagram of S/N ratio, it is evident that the maximal value appears when the photodetection polarizing angle is 20° in case of Al 8000. In case of Poly 3000, the maximal value appears when the photodetection polarizing angle is 30°. The position of the maximal value obtained in FIG. 5 is deviated from the photodetection polarizing angle of the maximal value of the PSL particle scattering output obtained in FIG. 3, and it is not necessarily consistent with one of the minimal value of the wafer surface scattering output. Further, the maximal value appears only at one point.

Therefore, in case of Al 8000, for instance, if the photodetection polarizing angle of the polarizing plate 26 is set to 20° and surface inspection is performed on the element to be inspected (wafer), the inspection can be carried out under the condition where the S/N ratio is at the highest, and inspection accuracy is also higher.

When the change associated with the photodetection polarizing angle is processed by signal processing—not only with respect to the surface scattering reflection output of the wafer but also with respect to the scattering reflection output of PSL particles, the results shown in FIG. 3 and FIG. 4 (and further, the results shown in FIG. 5) are obtained. Thus, it is possible to obtain the photodetection polarizing angle of the polarizing plate 26 where the S/N ratio reaches at the highest.

When the photodetection polarizing angle of the polarizing plate 26 is determined, the photodetection polarizing angle setting motor 31 is rotated at every preset angle by the arithmetic unit 28. PSL particles scattering output and wafer surface scattering output at each preset angle of the polarizing plate 26 are calculated. Further, at the arithmetic unit 28, an angle of the polarizing plate 26 at the maximal value of the S/N ratio is stored in memory, and this angle is used in actual surface inspection.

The noise and the signal are included in the photodetection output of the second photodetection sensor 24, which is obtained by projecting the laser beam to the surface of the wafer 2. As described above, when the polarizing plate 26 is rotated and the photodetection polarizing angle is changed, the S/N ratio on the photodetection output is changed.

The condition of S/N ratio of the photodetection output obtained by using the wafer for calibration, i.e. noise removing condition, is confirmed in histogram.

Figure 6:
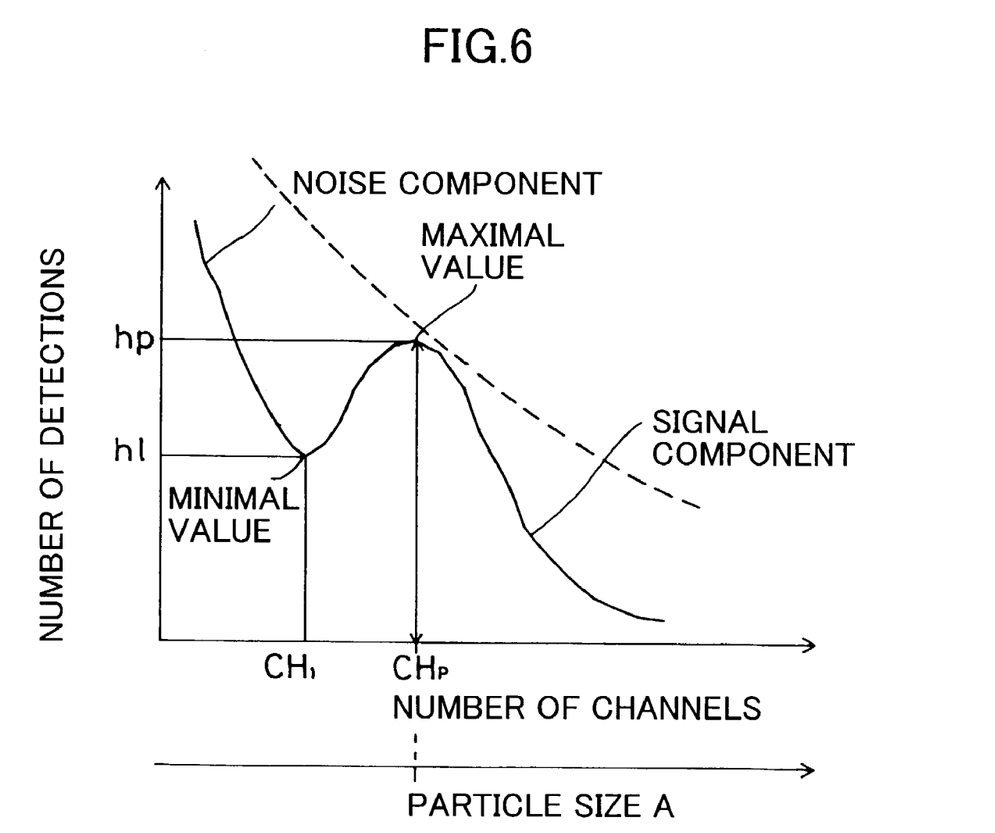
FIG. 6 is a diagram showing a histogram curve.

In FIG. 6, particle sizes of foreign objects is represented on the axis of abscissa, and number of detections of the foreign objects are given on the axis of ordinate. The particle size A shown in the diagram is that of the particle coated on the wafer for calibration.

In FIG. 6, a curve shown by solid curve (called "histogram curve") shows the case where the polarizing plate 26 is set to a rotating position where the S/N ratio is at the highest.

Under the condition where the S/N ratio is at the highest, the noise is removed, and the peak value appears at the particle size A. With the decrease of particle size, it is gradually decreased. After the minimal value appears, it is increased. The minimal value indicates the boundary between the particle size detection signal and the noise. The signal after appearance of the minimal value (i.e. number of detections) is the noise component. That is, when the S/N ratio is increased, and the noise component and the signal component are separated from each other, the minimal value and the maximal value appear. Also, the position of the maximal value shows the particle size of the particle already known.

Although not shown in the figure, by the rotation of the polarizing plate 26, the S/N ratio of the photodetection output is changed, and this histogram curve is also changed. When the polarizing plate 26 is rotated from the condition shown by the solid line in FIG. 6, the noise component in the photodetection output is increased, and the noise removing condition becomes worse. As a result, difference between the maximal value and the minimal value is decreased on the histogram curve. The extreme condition with higher noise component is shown by a dotted line in FIG. 6.

Therefore, if the polarizing plate 26 is rotated at every preset angle and a histogram line is obtained at every rotating position, and if the rotating position of the polarizing plate 26 where the maximal value and the minimal value most remarkably appear on the histogram curve is obtained, it is a position where the S/N ratio at the rotating position is at the highest.

Besides the condition where the S/N ratio of the photodetection output is at the highest, if it is supposed that number of detections at the minimal value is hl, and number of detections at the maximal value is hp, it may be judged that the S/N ratio is at the highest when the value of hl/hp is about 0.7 or more.

The rotating position of the polarizing plate 26 is determined in such manner that the value of hl/hp is approximately 0.7 or more.

When the rotating position of the polarizing plate 26 is determined, surface inspection is performed on the wafer 2 to be inspected. Because the S/N ratio of the photodetection output is set to the highest, it is possible to carry out the surface inspection with high accuracy.

Figure 7:
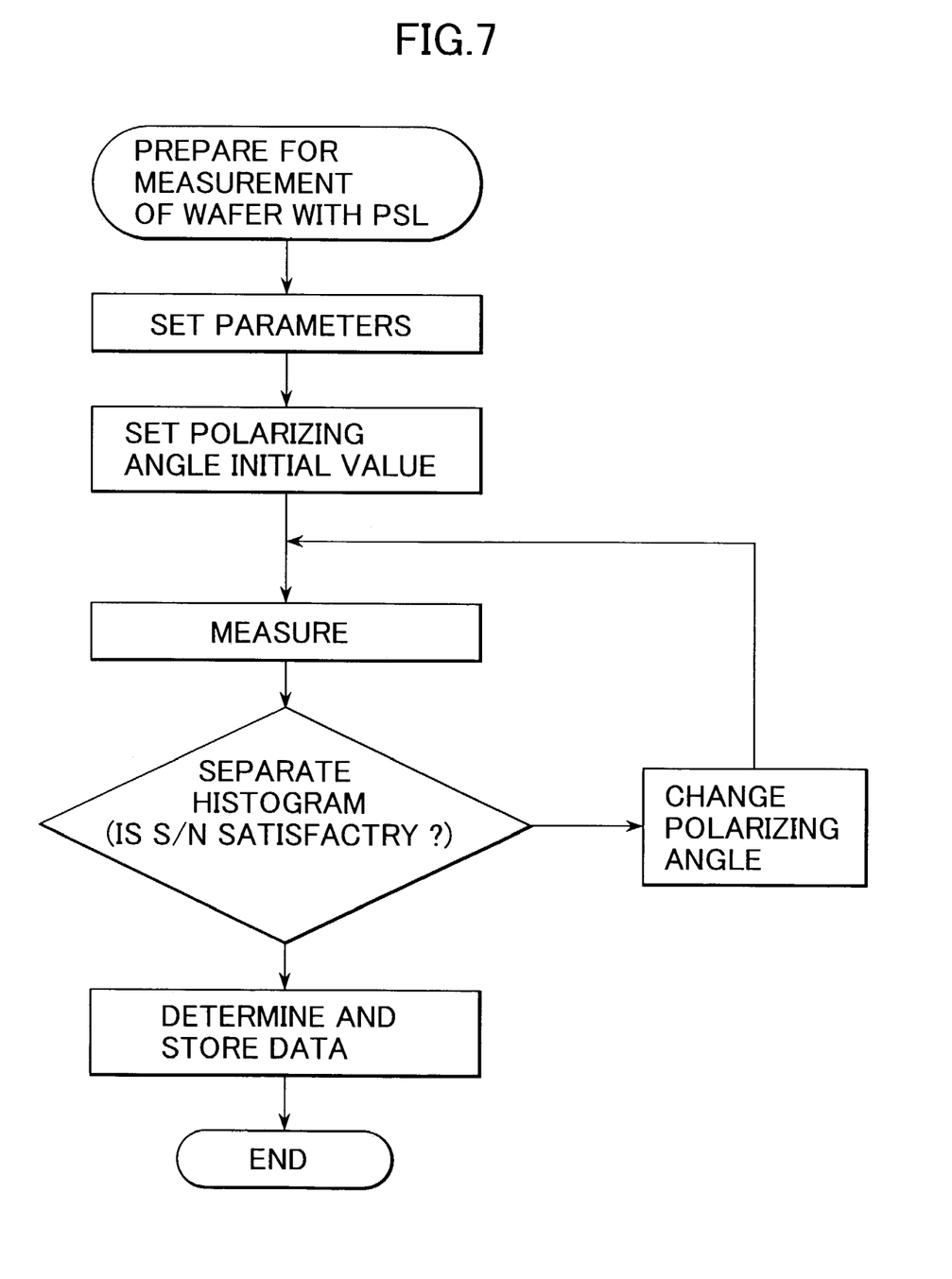
FIG. 7 is a flow chart showing a process for setting the inspecting conditions.

Now, description will be given on the inspecting condition setting process referring to FIG. 7.

The wafer 2 with PSL particles (standard particles) coated on it is retained by the wafer chuck 3.

From the operation panel 35, parameters necessary for surface inspection (such as type of film formed on the wafer surface, particle size to be measured, and projecting intensity of the laser beam) are set.

An initial photodetection polarizing angle is set.

The laser beam is projected, and the wafer 2 is rotated and moved by sliding. The entire surface of the wafer is scanned, and measurement is performed.

From the results of measurement, a histogram is prepared. Noise removing condition is obtained. It is judged whether the value hl/hp is about 0.7 or more or not, for instance. If hl/hp<0.7, the photodetection polarizing angle is rotated at a predetermined angle by rotation of the photodetection polarizing plate 26, and the surface inspection is performed again.

In the removing condition, if hl/hp>0.7 or more, for instance, the photodetection polarizing angle at this moment is stored, and the inspection condition setting process is terminated.

Actual surface inspection is carried out when the polarizing plate 26 is held at the photodetection polarizing angle thus obtained.

In the present invention, the position of the polarizing plate 26 is set under the condition where the S/N ratio of actual photodetection output is at the highest regardless of film quality and film thickness, and surface inspection is performed. As a result, it is possible to carry out the surface inspection with high accuracy even to the wafer 2 which has film quality and film thickness of unknown characteristic.

In order to change of the photodetection polarizing angle, instead of the rotation of the polarizing plate, an optical element such as liquid crystal polarizing filter using liquid crystal, etc. may be used, which can electrically perform rotation control of the plane of polarization.

The present invention provides a surface inspection method in a surface inspection system, which comprises a photodetection unit and a photodetection polarizing angle changing means, comprising the step of receiving a scattered reflection light from a substrate surface where standard particles are coated by changing a photodetection polarizing angle by the photodetection polarizing angle changing means, and the step of performing surface inspection by setting the photodetection polarizing angle to a condition where an S/N ratio of photodetection output is at the highest. As a result, surface inspection can be carried out under the condition where S/N ratio of the photodetection output is at the highest regardless of film quality and film thickness, and surface inspection with high accuracy can be carried out even to the surface of a substrate which has surface property of unknown characteristic.

What is claimed is:

1. A surface inspection method in a surface inspection system which comprises a projection optical system for projecting two or more inspection lights at different incident angles to a substrate surface, a photodetection unit for detecting the inspection lights reflected from said substrate surface, and for detecting scattered reflected inspection lights, said photodetection unit comprising a photodetection polarizing angle changing means for changing a photodetection polarizing angle of said photodetection unit, comprising:

a step of obtaining a signal component in a photodetection signal based on photodetection results when inspection lights are projected by changing incident angles, step of receiving a scattered reflection light from said substrate surface where standard particles are coated by changing a photodetection polarizing angle by said photodetection polarizing angle changing means, a step of obtaining the highest value of an S/N, signal to noise, ratio of photodetection output when the minimal value and the maximal value in a histogram are clearly separated from each other, and a step of performing surface inspection by setting the photodetection polarizing angle to a condition where the S/N ratio of photodetection output is at the highest.

2. A surface inspection method according to claim 1, wherein it is judged that the S/N ratio is the highest value when a ratio of the minimal value to the maximal value is 0.7 or more.

3. A surface inspection system, comprising a projecting optical system for projecting two or more inspection lights to a surface to be inspected at different incident angles, a photodetection unit for detecting the inspection lights reflected from the surface to be inspected, and an arithmetic unit, wherein said photodetection unit detects scattered reflection light of the inspection lights which are projected at different incident angles, and said photodetection unit comprises a photodetection polarizing angle changing means for changing a photodetection polarizing angle of said photodetection unit, and a noise component and a signal component can be obtained based on photodetection results of scattered reflection lights of said inspection lights which are projected at different incident angles, and an S/N, signal to noise, ratio of photodetection output can be changed by said polarizing angle changing means, and wherein said arithmetic unit obtains a histogram at each photodetection polarizing angle respectively by changing the photodetection polarizing angle, calculates a point where a ratio of the minimal value to the maximal value is at the highest by comparing the obtained histograms with each other, and calculates the photodetection polarizing angle of said photodetection polarizing angle changing means.

4. A surface inspection system according to claim 3, wherein it is judged that the S/N ratio is the highest when a ratio of the minimal value to the maximal value is 0.7 or more.

* * * * *

UNITED STATES PATENT AND TRADEMARK OFFICE
CERTIFICATE OF CORRECTION

PATENT NO.         : 7,064,820 B2
APPLICATION NO. : 10/393833
DATED              : June 20, 2006
INVENTOR(S)        : Hisashi Isozaki et al.

It is certified that error appears in the above-identified patent and that said Letters Patent is hereby corrected as shown below:

Title Page

Please add the following Assignee:

--(73) Assignee: Fujitsu Limited, Kanagawa (JP)--

Signed and Sealed this

Twelfth Day of February, 2008

JON W. DUDAS
*Director of the United States Patent and Trademark Office*